US 6,735,368 B2

(12) United States Patent
Parker et al.

(10) Patent No.: US 6,735,368 B2
(45) Date of Patent: May 11, 2004

(54) OPTICAL DELAY DEVICE

(75) Inventors: Gregory J. Parker, Hampshire (GB); Martin D. B. Charlton, Southampton (GB); Majd Zoorob, Southampton (GB)

(73) Assignee: Mesophotonics Limited, Southampton (GB)

( * ) Notice: Subject to any disclaimer, the term of this patent is extended or adjusted under 35 U.S.C. 154(b) by 0 days.

(21) Appl. No.: 10/438,316

(22) Filed: May 15, 2003

(65) Prior Publication Data

US 2003/0228096 A1 Dec. 11, 2003

Related U.S. Application Data

(63) Continuation-in-part of application No. 10/147,328, filed on May 17, 2002, which is a continuation-in-part of application No. 09/910,014, filed on Jul. 23, 2001, now Pat. No. 6,640,034, which is a continuation of application No. 09/663,443, filed on Sep. 15, 2000, now abandoned, which is a continuation of application No. 09/415,233, filed on Oct. 12, 1999, now abandoned, which is a continuation of application No. PCT/GB98/01429, filed on May 18, 1998.

(30) Foreign Application Priority Data

May 16, 1997 (GB) .............................................. 9710062

(51) Int. Cl.[7] .............................. G02B 6/12; H04J 14/00
(52) U.S. Cl. ........................... 385/122; 385/14; 385/15; 385/24; 385/37; 385/129; 385/130; 385/131; 385/1; 385/2; 385/8; 398/51; 398/53; 398/54; 398/81; 398/84; 398/87
(58) Field of Search ........................... 385/122, 14, 15, 385/24, 37, 129, 130, 131, 1, 2, 8; 398/51, 53, 54, 81, 84, 87

(56) References Cited

U.S. PATENT DOCUMENTS

| 4,894,726 A | 1/1990 | Steinhardt et al. ........... 356/298 |
| 5,526,449 A | 6/1996 | Meade et al. .................. 385/14 |
| 5,651,079 A | 7/1997 | Goorjian ....................... 385/16 |
| 5,682,401 A | 10/1997 | Joannopoulos et al. ....... 372/96 |

(List continued on next page.)

FOREIGN PATENT DOCUMENTS

| EP | 0 836 112 A2 | 4/1998 | ................. 385/129 |
| EP | 0123456 A2 | 1/2000 | ............... 385/14 X |
| EP | 1 024 378 A2 | 8/2000 | .................. 385/24 |
| EP | 1 168 008 A2 | 1/2002 | .................. 385/24 |
| EP | 1 205 788 A1 | 5/2002 | ................. 385/123 |
| WO | 94/16345 A | 7/1994 | ............... 385/14 X |
| WO | WO 02/14913 A1 | 2/2002 | ................. 385/129 |
| WO | WO 02/25781 A2 | 3/2002 | ................. 385/129 |

OTHER PUBLICATIONS

Krauss et al, "Optical Characterization of Waveguide Based . . .," vol. 68, No. 12, pp. 1613–1615 (1996).

Kosaka et al, "Photonic Crystals for Micro Lightwave Circuits Using Wavelength–Dependent Angular Beam Steering" *Applied Physics Letters*, vol. 74, No. 10, Mar. 1999, pp. 1370–1372.

Agio et al, "Impurity Modes in a Two–Dimensional Photonic Crystal: Coupling Efficiency and Q Factor" *J. Opt. Soc. Am*, vol. 17, No. 12, Dec. 2000, pp. 2037–2042.

(List continued on next page.)

*Primary Examiner*—Brian M. Healy
(74) *Attorney, Agent, or Firm*—Nixon & Vanderhye P.C.

(57) ABSTRACT

An optical system includes a delay region having a photonic band structure, a modulated optical signal source, an optical input, and an optical output. The optical input couples modulated input optical signals into a predetermined mode in the delay region such that group velocity of the optical signal is reduced. The optical output includes a wavelength selective element. Input optical signals are coupled into a highly dispersive mode in the delay region in which the group velocity of the optical signal is reduced. The input signal, which has been delayed and dispersed, is recovered at the output of the device using the wavelength selective element.

36 Claims, 10 Drawing Sheets

U.S. PATENT DOCUMENTS

| | | | |
|---|---|---|---|
| 5,748,057 A | 5/1998 | De Los Santos | 333/134 |
| 5,751,466 A | 5/1998 | Dowling et al. | 359/248 |
| 5,802,236 A | 9/1998 | DiGiovanni et al. | 385/127 |
| 5,963,683 A | 10/1999 | Goorjian | 385/16 |
| 5,973,823 A | 10/1999 | Koops et al. | 359/322 |
| 5,978,530 A | 11/1999 | Russell et al. | 385/37 |
| 5,987,208 A | 11/1999 | Gruning et al. | 385/146 |
| 6,002,522 A * | 12/1999 | Todori et al. | 359/573 |
| 6,028,693 A | 2/2000 | Fork et al. | 359/248 |
| 6,134,043 A | 10/2000 | Johnson et al. | 359/237 |
| 6,134,369 A | 10/2000 | Kurosawa | 385/132 |
| 6,175,671 B1 | 1/2001 | Roberts | 385/14 |
| 6,278,105 B1 | 8/2001 | Mattia | 250/214.1 |
| 6,310,991 B1 | 10/2001 | Koops et al. | 385/14 |
| 6,334,017 B1 | 12/2001 | West | 385/123 |
| 6,396,617 B1 * | 5/2002 | Scalora | 359/248 |
| 6,466,703 B1 * | 10/2002 | Ionov | 385/10 |
| 6,640,034 B1 * | 10/2003 | Charlton et al. | 385/122 |
| 2002/0021878 A1 | 2/2002 | Allan et al. | 385/14 X |

OTHER PUBLICATIONS

Kosaka et al, "Superprism Phenomena in Photonic Crystals: Toward Microscale Lightwave Circuits" *Journal of Lightwave Technology*, vol. 17, No. 11, Nov. 1999.

Mogilevtsev et al, "Group–Velocity Dispersion in Photonic Crystal Fibers" *Optics Letters*, vol. 23, No. 21, Nov. 1998, pp. 1662–1664.

O'Brien et al, "Lasers Incorporating 2D Photonic Bandgap Mirrors" *Electronics Letters*, vol. 32, No. 24, Nov. 1996.

Lee et al, "Microcavities, Photonic Bandgaps and Applications to Lasers and Optical Communications" IEEE, 1999.

Kosaka et al, "Superprism Phenomena in Photonic Crystals" *Physical Review B*, vol. 58, No. 16, Oct. 1998.

Hosomi et al, "A Dispersion Compensator Using Coupled Defects in a Photonic Crystal" *IEEE Journal of Quantum Electronics*, vol. 38, No. 7, Jul. 2002, pp. 825–829.

Meltz et al, "Bragg Grating Formation and Germanosilicate Fiber Photosensitivity" International Workshop on Photoinduced Self–Organization Effects in Optical Fiber, SPIE vol. 1516, Oct. 1991, pp. 185–199.

Gaponenko et al, "Spontaneous Emission of Dye Molecules, Semiconductor Nanocrystals, and Rare–Earth Ions in Opal–Based Photonic Crystals" *Journal of Lightwave Technology*, vol. 17, No. 11, Nov. 1999, pp. 2128–2137.

Benisty et al, "Radiation Losses of Waveguide–Based Two–Dimensional Photonic Crystals: Positive Role of the Substrate" *Applied Physics Letters*, vol. 76, No. 5, Jan. 2000, pp. 532–534.

Koops et al, "Two–Dimensional Photonic Crystals Produced by Additive Nanolithography with Electron Beam–Induced Deposition Act as Filters in the Infrared" *Microelectronic Engineering*, 57–58, 2001, pp. 995–1001.

Krauss et al, "Photonic Crystals in the Optical Regime–Past, Present and Future" *Progress in Quatum Electronics*, vol. 23, 1999, pp. 51–96.

Cao et al, "Microlaser Made of Disordered Media" *Applied Physics Letters*, vol. 76, No. 21, May 2000, pp. 2997–2999.

Jin et al, "Band Gap and Wave Guiding Effect in a Quasi-periodic Photonic Crystal" *Applied Physics Letters*, vol. 75, No. 13, Sep. 1999, pp. 1848–1850.

XP–002226009, "466/OFC 2002/Thursday Morning" Mar. 2002, pp. 466–468.

Birks et al.; "Full 2–D Photonic Bandgaps in Silica/Air Structures", Electronics Letters, IEE Stevenage, GB vol. 31, No. 22, Oct. 26, 1995, pp. 1941–1943, XP000543391; ISSN: 0013–5194.

Koops, Hans W.P.; "Photonic Crystals Built By Three–Dimensional Additive Lithography Enabled Integrated Optics of High Density", Proceedings of the SPIE, SPIE, Bellingham, VA, US, vol. 2849, Aug. 5, 1996, pp. 248–256, XP000617864.

* cited by examiner

OPTICAL DELAY DEVICE

CROSS-REFERENCE TO RELATED APPLICATIONS

This application is a Continuation-in-Part of U.S. patent application Ser. No. 10/147,328, filed on May 17, 2002, which is a Continuation-in-Part of U.S. patent application Ser. No. 09/910,014, filed on Jul. 23, 2001, now U.S. Pat. No. 6,640,034, which is a continuation of U.S. patent application Ser. No. 09/663,443, filed on Sep. 15, 2000, now abandoned, which is a continuation of U.S. patent application Ser. No. 09/415,233, filed Oct. 12, 1999, now abandoned, which is a continuation of PCT/GB98/01429, filed May 18, 1998, which claims priority to U.K. Application No. 9710062.2, filed May 16, 1997, the entire content of which is hereby incorporated by reference in this application.

FIELD OF THE INVENTION

The present invention relates to the field of optical signal processing using photonic structures and in particular to optical signal delay elements.

BACKGROUND

Communications and data processing are increasingly being performed optically. Optical systems are faster than their electrical equivalents and allow for greater data throughput. However, electrical elements are still needed at present to provide data storage and appreciable signal delay. Signal delay is important for a number of data processing applications in data transmission, encryption and processing.

Periodic dielectric structures have been fabricated which exhibit photonic properties analogous in many respects to the electronic properties of semiconductors. A periodic variation in refractive index can give rise to a photonic band structure in which only certain photonic states are allowed.

This is most easily observed in the formation of a photonic band gap. Structures exhibiting a photonic band gap forbid the transmission of light in a particular range of frequencies. Structures of this sort are disclosed in WO94/16345 and WO98/53351.

Photonic bandgap (PBG) structures can be formed by a slab of dielectric material having a periodic array of regions having a different refractive index. Holes can be drilled or etched into the material, or an array of columns can be formed. Alternatively, stacks of dielectric material of alternating refractive index or a series of slots cut into a dielectric substrate can be used to form a 1-dimensional photonic crystal. The properties of the band structure and in particular the response to different frequencies of light are determined by the properties of the materials and by the geometry of the structure.

Examples of the applications of photonic band structures include the formation of waveguides, use in lasing devices, sensors and even in optical multiplexers and demultiplexers.

SUMMARY OF THE INVENTION

According to one aspect of the invention an optical system comprises: a modulated optical signal source; an optical input; a delay region having a photonic band structure; and an optical output; wherein the optical input is adapted to couple an input optical signal of a particular wavelength from the modulated optical signal source into a predetermined mode in the delay region such that the group velocity of the optical signal is reduced; and wherein the optical output includes a wavelength selective element to select said particular wavelength.

Modulated input optical signals are coupled into a highly dispersive mode in the delay region in which the group velocity of the optical signal is reduced. The group velocity is the velocity of each optical packet, i.e. the velocity of the optical data. The input signal, which has been delayed and dispersed, is recovered at the output of the device using the wavelength selective element. Input signals with data encoded on a plurality of different wavelengths can be used and each wavelength selected at the output.

Without a wavelength selective element the modulated optical output signal is extremely distorted. The finite packet length of the modulated optical signal gives rise to signal broadening of the transmission wavelength of the optical signal and a band of frequencies will be contained within each packet. The highly dispersive nature of the delay region spreads the frequency content of an input optical packet giving rise to a messy output. The processing performed by the wavelength selective element results in the realisation of a delayed output corresponding to the input signal. The delayed output may be attenuated but it is possible to provide improved transmittance by the use of optical amplification.

Different frequencies within each optical packet will experience dispersion and hence will be delayed and spatially shifted by different amounts in the delay region. The delay region can therefore be considered to process the input signal both spatially and temporally. The recovery of the correct signal can be achieved using either one of these properties i.e. the wavelength selective element may select wavelength spatially or temporally. In the case where the input signal is incident at an angle to normal to the input face of the delay region, the wavelength selective element in the optical output can simply be a correctly positioned output waveguide. This is because the dispersion within each packet will refract different parts of the packet through different angles corresponding to the refraction of different wavelengths. Separate spatial wavelength selection may be achieved through mechanisms such as filtering, refraction, diffraction and interference. Temporal wavelength selection takes advantage of the fact that different wavelengths undergo a different delay. The output signal can therefore be gated to separate different wavelengths.

If a continuous light beam of a single frequency is launched into a photonic band structure and coupled into a dispersion mode only a single wavelength is output, rendering wavelength selection unnecessary. Moreover, a continuous beam has no group velocity as such and so no delay is realised except for that experienced by the phase velocity variation in the photonic structure and material. However, if a modulated optical signal, which necessarily contains a spread of wavelengths, is launched into a photonic band structure the resulting output is so distorted that it is impossible to tell that any part of the signal has been delayed. The output appears to be a meaningless mess. The provision of a wavelength selective element at the output extracts a useful output from the mess.

The temporal and spatial separation of the optical signal also results in power being lost at the output. During post-processing only a fraction of the input signal can be collected and hence loss is experienced. If more loss can be tolerated, it will provide for greater delays.

Preferably, the delay region comprises a first material having a first refractive index including an array of regions having a second refractive index. Preferably, the array extends over a plane in two dimensions. Alternatively, the delay region may be a 1 dimensional photonic crystal formed from a stack of dielectric slabs with alternate slabs forming the array of regions having a second refractive index, or a series of slots cut into a substrate material.

The array of regions having a second refractive index gives rise to a photonic band structure. The characteristics of the band structure are dependent on the geometry and material properties of the array of regions. The frequency response of the delay region is therefore dependent on the geometry and material properties of the array of regions.

Preferably, the array has a low order of symmetry. In particular, the order of rotational symmetry about a point in the array is preferably less than four. A lower order of symmetry gives rise to a less uniform band structure, i.e. a more rapid variation of frequency with wave vector. This gives rise to a greater rate of change of group velocity around the band edges.

Preferably, the array of regions includes one or more defects. This allows the band structure to be tuned more easily as it gives rise to a high Q-factor for the array. The defect could, for example, be a missing region in the array, a displaced region or an enlarged or reduced region within the array. Alternatively, it could be a region within the array having a different refractive index to the rest of the array.

Preferably, the defect is formed from a superposition of two arrays. The superposition of lattices results in a Moire type structure which responds in a similar manner to a set of defects introduced into a single array and is easier to design. Having a set of defects allows light to be coupled into a defect mode more easily than for a single defect. Furthermore, having a large number of defects introduces flat bands in the band structure which allows greater optical delays to be achieved more readily.

Preferably, the finite bandwidth of the optical signal lies in an optimised flat region of the dispersion band, so that most of the delayed signal travels at a similar group velocity. This is also beneficial in reducing the amount of energy lost to other dispersed wavelengths in the optical signal, as they will be removed by a post processing scheme.

Preferably, the first material is silicon nitride or silicon oxynitride.

The delay region may be adapted to allow the transmission of optical signals therethrough, but preferably is adapted to predominantly reflect optical signals of a particular wavelength of operation.

The frequency response of the delay region may be tuned by varying the temperature of the delay region. This causes expansion or contraction of the delay region and hence alters the geometry of the array. Alternatively a piezoelectric material could be used.

Alternatively, the frequency response of the delay region may be tuned by altering the refractive index structure of the delay region. This can be achieved by changing the material composition of the regions, for example when the array of regions is formed from an array of holes in a slab of material, the composition of the material filling the holes can be varied. It can also be achieved by forming either the first material or the array of regions from an electro-optic or magneto-optic material and applying a potential difference or magnetic field across the delay region.

The direction of incidence of optical signals relative to the array can be altered to obtain a different frequency response from the delay region. Preferably, this is achieved by rotation of the delay region relative to the optical input and optical output.

Preferably, the optical system is adapted to cause optical signals from the input to undergo multiple passes of the delay region. The greater the optical path length within the delay region the greater the delay on the optical signal.

The optical system may be adapted such that an input optical signal undergoes a plurality of passes through a delay region. The optical system may also include multiple delay regions. Input optical signals would then pass through each delay region in turn at least once.

Preferably, the optical system includes a delay region and waveguides, the waveguides causing multiple passes of input optical signals through the delay region.

More preferably, the optical system includes two delay regions arranged parallel to one another, each adapted to reflect the input optical signals toward the other, such that, in use, input optical signals undergo a plurality of reflections before reaching an optical output. Preferably, waveguides are positioned between the two delay regions to receive the reflected signals. The delay regions may be stacks of dielectric slabs of alternating refractive index arranged parallel to one another or parallel slots cut into a first material filled with a second material.

The wavelength selective element may be a simple optical filter.

The optical system may be adapted so that the delay region diffracts optical signals as well as reducing their group velocity. The optical output or outputs can then be placed at particular angular positions to receive particular orders of diffraction. The use of a diffracted beam as an output signal provides automatic wavelength selection. The delay region thus acts as the wavelength selective element. This combined functionality is achieved by matching the effective grating pitch of the delay region to the wavelength of operation whilst also coupling the input signals into a suitable mode. The optical input may be arranged at an angle to an input or output facet of the delay region so that the input optical signal is refracted. Owing to the dispersive nature of the delay region, different wavelengths travel at different speeds within it and hence will refract through different angles. Therefore, by positioning the optical output to receive light refracted at a particular angle, wavelength selection is achieved. With the input at an angle to the input facet of the delay region, the input optical signal is refracted at the input facet to spatially separate different wavelengths at the output facet. With the input normal to the input facet but at an angle to the output facet the signal is refracted at the output to angularly separate different wavelengths at the output facet.

The optical system may form part of a phase-arrayed waveguide grating. The delay region is positioned in an input star coupler or a Multi-Mode Interference (MMI) region whilst the outputs of the arrayed waveguides diffract the light into a specific output waveguide in a star coupler type arrangement.

Alternatively, the wavelength selective element may be an optical gate adapted to sample an optical output at different times. The sampling rate is dependent on the bit rate of the input optical signal.

According to a second aspect of the present invention, an optical device comprises: an optical input, a delay region having a photonic band structure and an optical output, wherein the optical input is adapted to couple an input optical signal of a particular wavelength into a particular mode in the delay region such that the group velocity of the optical signal is reduced; and wherein the delay region is adapted to allow the input signal to be coupled into a highly dispersive mode to predominantly reflect the input optical signal from the delay region at the particular wavelength of operation.

According to a third aspect of the present invention, an optical device comprises: an optical input, a delay region having a photonic band structure and an optical output, wherein the optical input is adapted to couple input optical signals into a particular mode in the delay region such that the group velocity of the optical signal is reduced; and wherein the optical device is adapted to cause the optical signals from the input to undergo a plurality of passes through the delay region to thereby increase the optical path length of optical signals in the delay region.

The optical system may include two delay regions arranged parallel to one another, each adapted to reflect the input optical signals toward the other, such that, in use, input optical signals undergo a plurality of reflections before reaching an optical output.

According to a fourth aspect of the present invention a method of applying a delay to a modulated optical signal comprises the steps of:

coupling the optical signal into a particular mode in a photonic band structure; and, selecting a part of the optical signal output from the photonic band structure, the selection being made on the basis of wavelength.

The step of selecting a part of the optical signal output may include passing the optical signal output through an optical filter, passing the optical signal output through a diffraction grating or passing the optical signal output through an optical gate. Alternatively, the step of selecting a part of the optical signal output may include collecting an angular portion of the optical signal output.

BRIEF DESCRIPTION OF THE DRAWINGS

The foregoing and other objects, features, and advantages of the present invention may be more readily understood with reference to the following description taken in conjunction with the accompanying drawings.

Examples of optical devices in accordance with the present invention will now be described in detail with reference to the accompanying drawings, in which:

FIG. 9c shows an optimised design for the device of FIG. 9a;

FIG. 10b is a plot of time delay versus frequency for the device of FIG. 10a;

FIG. 12b shows an alternative to the device of FIG. 12a;

DETAILED DESCRIPTION

In the following description, for purposes of explanation and not limitation, specific details are set forth, such as particular example embodiments, procedures, techniques, components, etc. in order to provide a thorough understanding of the present invention. However, it will be apparent to one skilled in the art that the present invention may be practiced in other embodiments that depart from these specific details.

A brief summary of the considerations to be taken into account and the parameters that can be altered in a photonic crystal structure will first be given, followed by a detailed description of particular devices and designs in accordance with the invention.

Figure 1:
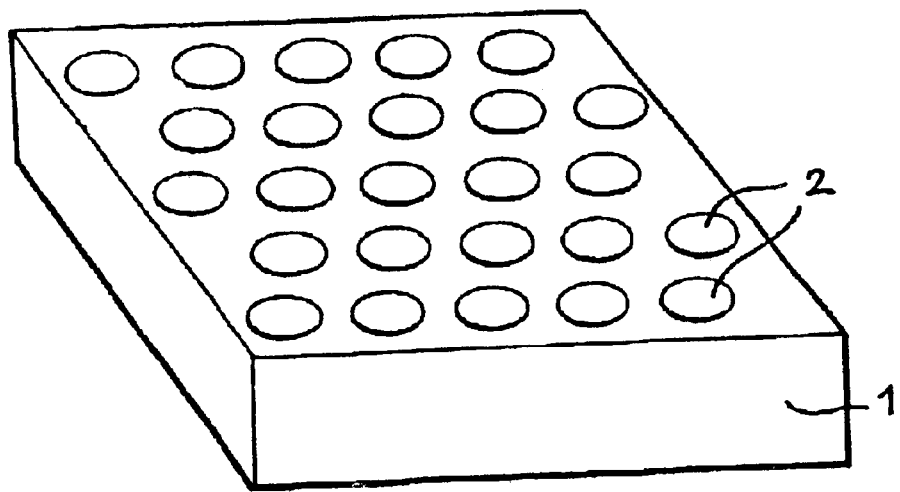
FIG. 1 shows a slab of dielectric material in which a lattice of air holes has been formed.
Figure 2:
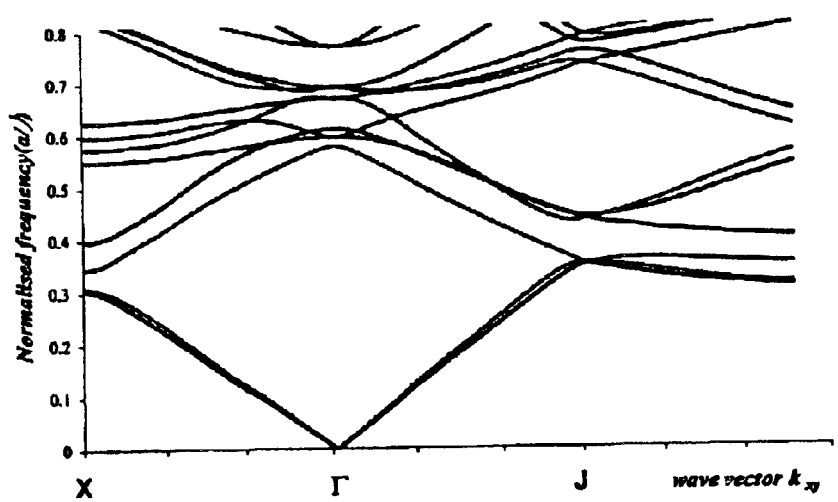
FIG. 2 is a plane wave band diagram for a silicon nitride structure having a lattice of air rods formed therein.

FIG. 1 shows a slab of dielectric material 1 in which a lattice of air holes 2 has been formed, suitable for use as a delay region in an optical delay element. The dielectric material is silicon nitride. The refractive index contrast between the dielectric slab and the air holes must be sufficient to create a photonic band structure. However, it is not necessary to create a complete band gap for the present invention and so relatively low index materials such as silicon nitride and silicon oxynitride can be used. The air holes 2 may be drilled into the slab but advantageously are etched. The array of air holes 2 gives rise to a photonic band structure as shown in FIG. 2. It is known how to fabricate structures of this type using drilling or etching.

FIG. 2 is a plane wave band diagram for the silicon nitride structure described above. The vertical axis is frequency and the horizontal axis is wave vector. The band diagram shows that the structure is highly dispersive, especially close to photonic bandgap/pseudo bandgap edges. The gradient of the lines on the band diagram determines the group velocity while the absolute value of ω/k determines the phase velocity. Therefore the group velocity of light at those specific frequencies close to the band edges is greatly reduced and may be zero if they optimally reach a point of inflection.

As stated above, it is not necessary to have a complete bandgap to obtain strong deviations in the group velocity. All that is required is that the frequency of operation is tuned to a specific band that is highly dispersive. Selecting a specific direction of propagation for the optical signal, for example the ΓX direction, provides an extra degree of freedom as partial bandgaps specific to the direction of propagation can be achieved.

Figure 3:
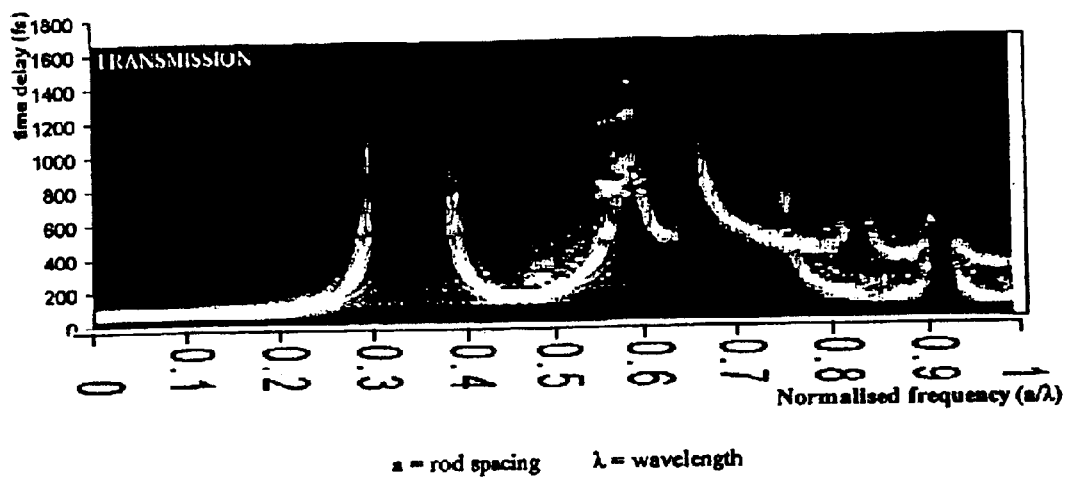
FIG. 3 is a plot of frequency versus time delay for a delay region formed from a slab of silicon nitride including an array of holes arranged in a triangular lattice structure, having 500 rows.

FIG. 3 is a plot of normalised frequency versus time delay for a delay region formed from a slab of silicon nitride including an array of holes arranged in a triangular lattice structure, having 500 rows. The optical signal is propagated along the ΓX direction. The results are obtained using a Finite-Difference Time Domain (FDTD) technique. The broadband light emerging from the photonic crystal material is collected and the frequency content is calculated with respect to time. This post-processing is necessary to filter the severe chirping effects arising from the dispersion. Similar post-processing will be described in more detail in relation to functional delay devices below.

The x-axis indicates the normalised frequency, which is scaled to the lattice pitch of the structure. The normalised frequency is equal to a/λ where a is the pitch of the lattice and λ is the wavelength of light. The y-axis indicates the relative time of arrival of different frequencies. The time scale does not give any indication of the absolute time of travel of the different frequencies through the structure. As can be seen, close to the band edges the change in the time of arrival increases dramatically. However the intensity of these signals are weaker owing to the difficulty in coupling into the modes close to the band edges as well as the distribution of the dispersed signal over a broad frequency band which amounts to loss once the output signal is filtered. A point of inflection on the band diagram giving zero group velocity is difficult to realise in practice as it lies just inside a band gap and so signals are not able to propagate through the structure.

It is clear that structures of this type can be used as dispersion compensators. If a suitable band is selected the dispersion of the structure can be used to cancel the dispersion properties of an optical fibre. The band structure can be tuned or optimised for a particular application through the choice of appropriate geometry and grading of geometry, material system, filling fraction, length and propagation direction.

The symmetry of a photonic crystal has a direct bearing on its band structure. The lower the symmetry of the crystal the greater the rate of change of group velocity with respect to frequency. This provides a means of varying the time delay of different frequencies simultaneously. This may be used, for example, in a dense wavelength division multiplexing (DWDM) application where many channels are equally spaced in wavelength. It has been found that a lattice structure having an order of symmetry of less than 4 is advantageous in practical applications, where in this context the order of symmetry is the order of rotational symmetry about a lattice point.

The absolute length of the photonic crystal structure is very important in determining the amount of delay imparted to an optical signal. The length of the photonic crystal is directly related to the maximum attainable time delay. The time delay scales linearly with the number of rows of the structure and hence longer structures can be used to achieve longer time delays. However, longer structures give rise to greater losses.

The response of the delay region can be tuned by a variety of methods. For example, heating the delay region causes expansion and hence an increase in the hole spacing. This directly affects the frequency response of the delay region. Another way to tune the delay region is to form it from a piezoelectric material and apply a voltage across it. This has the same expansive or contractive effect as a variation in temperature and hence affects the frequency response of the delay region. Alternatively, an electro-optic material could be used which has a refractive index which is responsive to applied voltage. A further possibility is to select a material to fill the holes forming the sub-array to have a particular refractive index in order to obtain a desired response. This can be done permanently or can be done dynamically using a variable composition fluid to fill the holes.

The introduction of defects into the delay region also affects the photonic band structure. The addition of a set of defects introduces flat bands and allows light to be more easily coupled into particular dispersion modes in the delay region. Sets of defects of this sort can be formed from the superposition of two regular lattices to from a Moire pattern. The Moire pattern behaves like a set of defects in a regular lattice.

The direction of propagation of an optical signal in the photonic crystal is also crucial to its frequency response as well providing the possibility for additional effects such as diffraction. The example in FIG. 3 is taken along the ΓX direction, which in a triangular lattice provides a primary band gap with no diffraction, as the wavelength of operation of the band gap is large compared with effective grating pitch. Propagation in the ΓJ direction in a triangular lattice introduces diffraction which can used to provide extra functionality. In delay devices the delay region may be fixed with respect to the optical input and outputs or may be rotatable relative to the optical input and outputs to provide a variable response.

Figure 4:
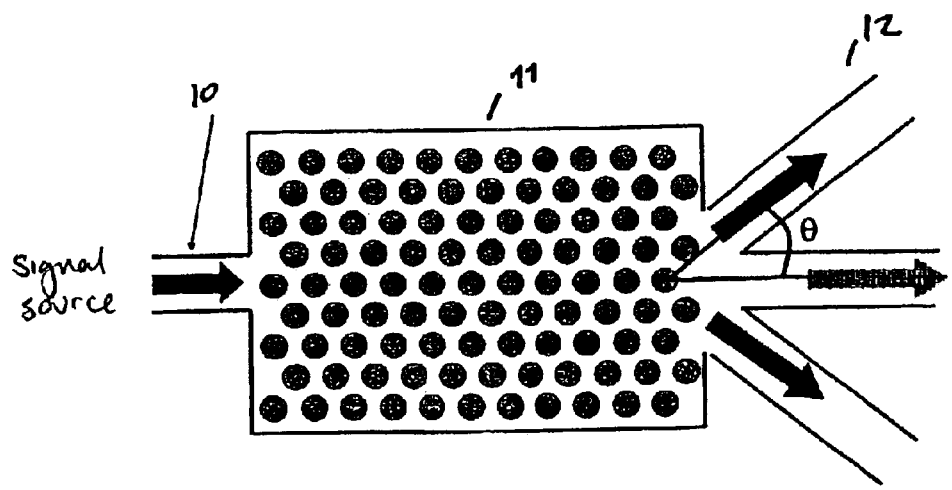
FIG. 4 is a schematic showing a delay system according to the present invention utilising diffraction.

The onset of diffraction could cause problems in time delay devices using the ΓJ direction owing to ghosting and interference of the signal by the diffraction when many channels are processed in parallel. Nevertheless, the first order diffraction can be used. The diffracted beams also experience a reduced group velocity and the use of a diffracted beam provides an automatic post-processing step. The beam is diffracted at a specific angle. The diffraction angle can be calculated and used as an output waveguide tilt angle. FIG. 4 shows a possible design for a device using this method. Modulated optical signals from a modulated optical signal source enter the device at input 10 and pass through the delay region 11. The signals are both delayed and diffracted in the delay region 11. Optical output 12 is positioned to receive the first order diffracted beam.

The use of photonic crystals having higher order of long range symmetry, such as quasi-crystals, allows an input signal to be split into many different signals using diffraction.

In order to use a photonic crystal structure as a delay region it is necessary to couple the optical signal to be delayed into a suitable mode in the delay region such that the group velocity of the signal is reduced. This requires that the wavelength of the signal and its direction of incidence with respect to the delay region be such that it is coupled into a dispersive mode in the delay region in which the signal has a reduced group velocity, i.e., a mode close to a point of inflection on the dispersion curve.

The use of time delay devices of this type in optical communications systems gives rise to further considerations owing to the packetised nature of the optical signals. In order to contain information optical signals must be modulated in some way and they are typically split into discrete packets. Each packet necessarily has a finite bandwidth, the shorter the packet the broader the bandwidth. Each frequency contained in an optical packet undergoes a different delay and, if input at an angle to normal incidence will undergo a different angular shift.

Figure 5:
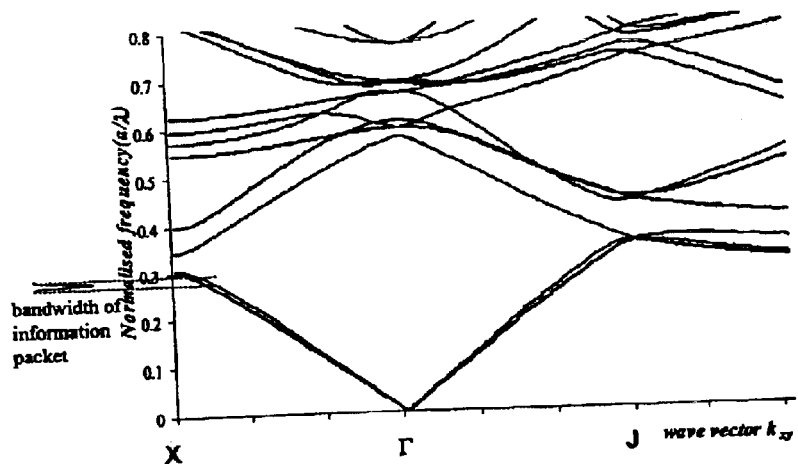
FIG. 5 is a band diagram showing the bandwidth of a packet of light carrying a single bit of information.

The bit rate of signals propagating through photonic crystal structures is also critical to its usefulness. Higher bit rate means shorter packets and broader bandwidth. It is vital that the bandwidth of each pulse is much narrower than the variation in the dispersion band at that point otherwise the signal is severely distorted in shape and cannot be identified. This is illustrated in FIG. 5.

Figure 6:
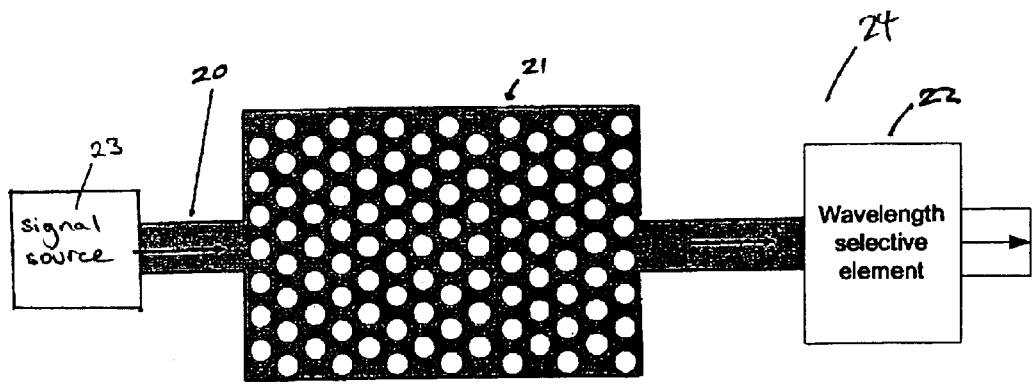
FIG. 6 illustrates a basic in-line delay system in accordance with the present invention.

The path length of the optical signal within the photonic crystal must be sufficient to provide an adequate time delay for the desired application. For relatively short time delays an in-line device may be suitable as is shown in FIG. 6. FIG. 6 shows schematically a system including a modulated optical signal source 23 an optical input 20, a delay region 21 and an optical output 24 including a wavelength selective element 22 which in this case is an optical filter.

Figure 7A:
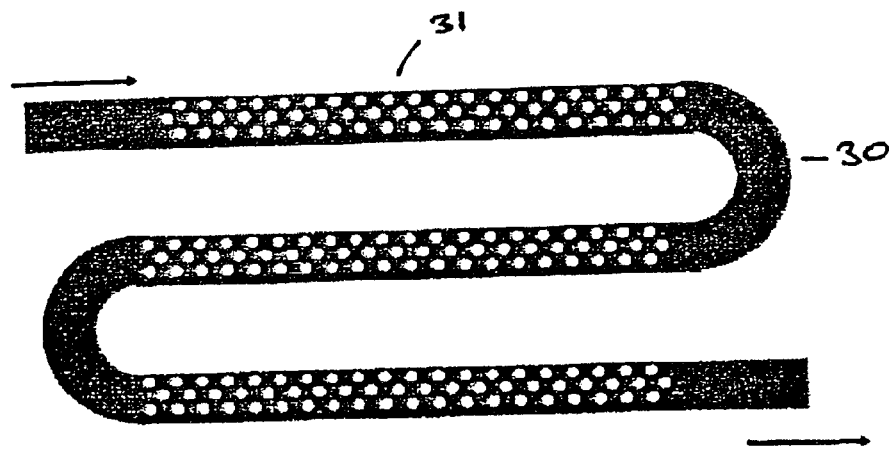
FIG. 7a illustrates an in-line device in accordance with the present invention comprising a bending waveguide including delay regions.

For longer time delays that might be required for dispersion compensation in a fibre, more complex designs can be used to keep the device compact. FIG. 7a shows a snaking waveguide 30 including regions of material 31 having a photonic band structure. The regions 31 are formed by an array of air holes in the waveguide material. The construction shown is such that the delay regions can be formed in a single slab with the waveguide 30 and waveguide bends subsequently formed. Modulated input optical signals are constrained within the waveguide 30 and thus pass through the delay region a plurality of times to give a relatively long optical path length within the delay region. The waveguide 30 can be formed in a conventional manner as described in Optical Waveguide Theory, by Allan Snyder and J. D. Love, Chapman & Hall.

Figure 7B:
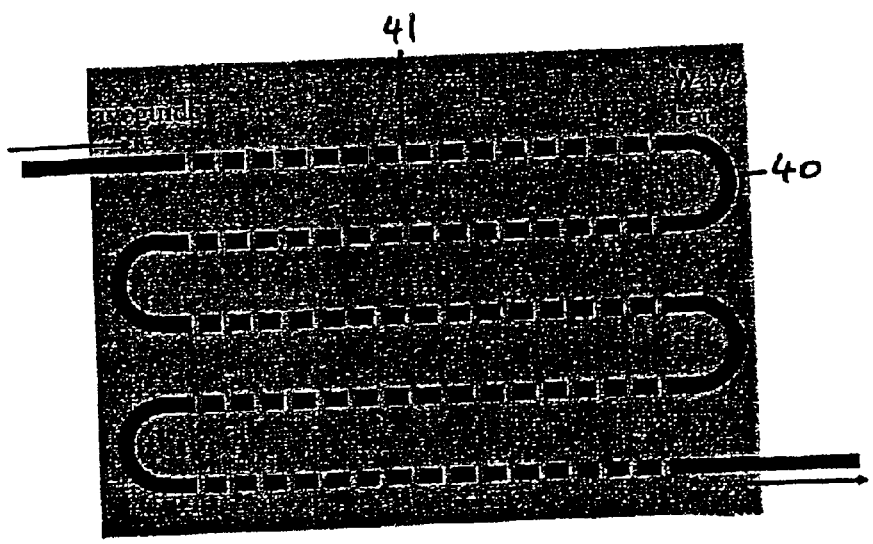
FIG. 7b illustrates a similar structure to FIG. 7a, wherein the delay regions are formed from slabs cut into the waveguide.

FIG. 7b shows a similar design with air channels 41 etched into a snaking waveguide 40. Alternative designs of the same type are possible. Very long path lengths in a small area can be obtained with a spiral design.

Figure 8:
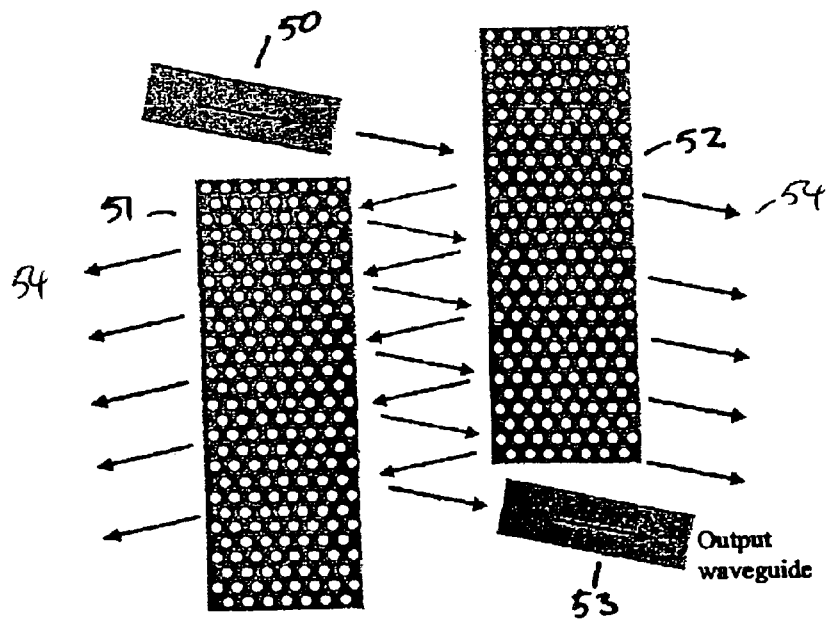
FIG. 8 shows an optical delay device according to the present invention using a reflection regime.

In a reflection scheme greater delays can be achieved than in transmission for a given loss of signal strength. A photonic band structure can be used in an etalon type structure. A device of this type is shown in FIG. 8. Modulated input optical signals are input from an input waveguide 50 at almost normal incidence to the delay regions 51,52 and undergo multiple partial reflections before reaching the output 53. The delay regions partially transmit at every reflection as shown by arrows 54. The wavelength selective element is not shown. By using photonic band structures in a reflection regime it is possible to couple input optical signals into a mode closer to a band edge than in a transmission regime. Close to a band edge transmission is attenuated severely. By contrast, tuning the input optical signals close to the band edge reduces losses due to multiple partial reflections in an etalon type structure. Thus it is possible to achieve a greater delay for a given path length in the delay region using a reflection regime and it is also possible to achieve a greater path length for a given loss.

Figure 9A:
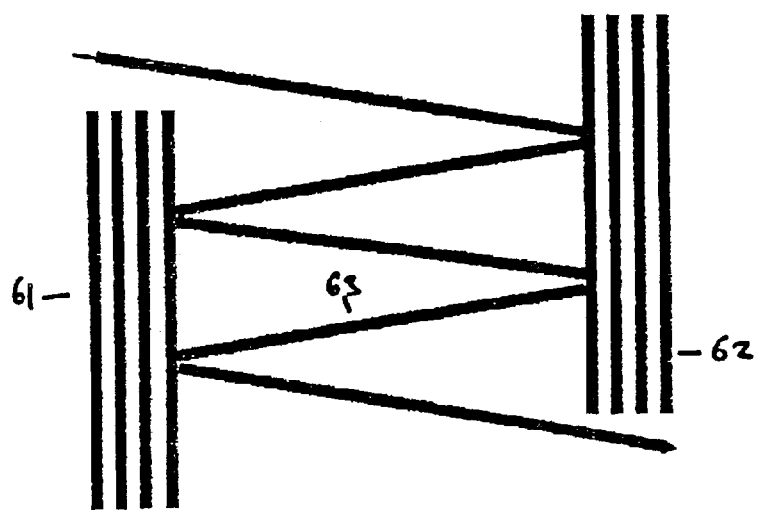
FIG. 9a shows a delay device using reflection, including waveguides between the two delay regions.

FIG. 9a shows waveguides formed between two dielectric stacks 61,62 which are in effect 1-dimensional photonic crystals. The difference in refractive index between adjacent layers of the stack is at least 10%. The stacks 61,62 give rise to a band structure and so can be used to introduce a time delay. The waveguides 63 reduce loss, which can be a major problem owing to the number of reflections required to produce long time delays.

Figure 9B:
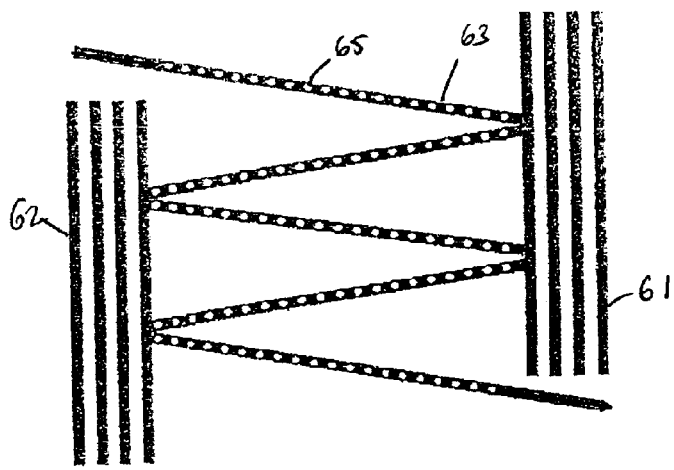
FIG. 9b shows a delay device similar in structure to the device of FIG. 9a but wherein the delay region is in the waveguides and the dielectric stacks are used for reflection.

Alternatively the structure of the dielectric stacks can be designed to give rise to a band gap at the frequency of operation to provide reflection of an optical signal, whilst the intermediate waveguides provide the delay in a transmission regime. This is illustrated in FIG. 9b. Clearly it is possible that optical delay could be provided both by the stacks in reflection and by delay regions 65 in transmission in intermediate waveguides.

Figure 9C:
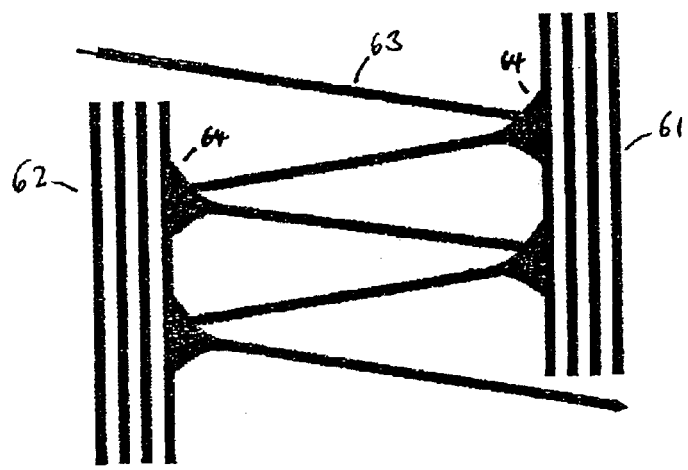

FIG. 9c shows an improved design for the device of FIG. 9a. Divergence spreads optical signals on incidence with the reflective stacks. The introduction of tapers 64 provides improved coupling into adjacent waveguides.

Figure 10A:
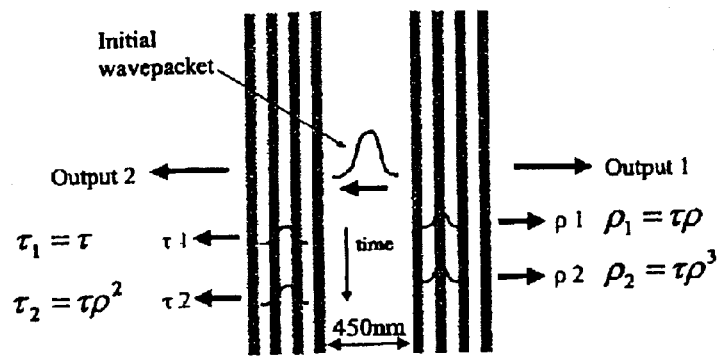
FIG. 10a illustrates the multiple outputs of a delay device using a reflection regime.
Figure 10B:
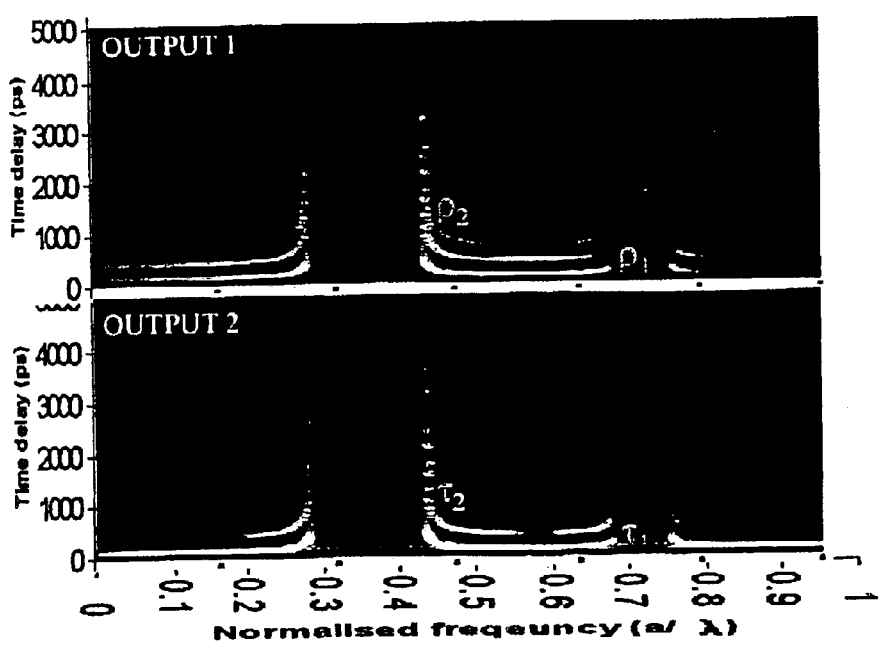

The structures of FIGS. 8 and 9 operate like an etalon in that for each reflection there will also be partial transmission. Thus there may be multiple output signals each with a different time delay. FIG. 10 illustrates schematically the time delay for each signal and FIG. 10b is a plot showing the time delay versus frequency. The reflective elements are dielectric stacks each having 100 rows. The dielectric used is silicon oxynitride. The distance between the two stacks is set at 450 mm. As can be seen in FIG. 10b there is an increase in the time delay with each reflection but there is also an associated decrease in intensity of the optical signal. For this reason the use of intermediate waveguides is highly beneficial.

A time delay or dispersion compensation device for modulated optical data signals using a photonic crystal as a highly dispersive region also requires a wavelength selective element at the output. A wavelength selective element is required in order to recover the input signal. This post processing can be achieved in a number of ways.

FIG. 4 shows perhaps the simplest way to provide the necessary wavelength selection. As described above, the input beam is both delayed and diffracted. Correct positioning of an output waveguide 12 allows the first order diffraction beam to be used as the output. The diffracted beam is necessarily wavelength separated and so the processing is achieved integrally with the delay region.

Figure 11:
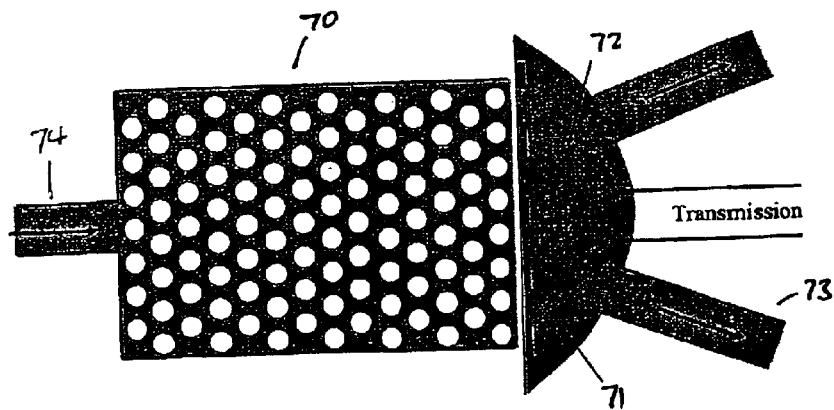
FIG. 11 shows an optical delay device according to the present invention including a diffraction grating at the optical output.

Alternatively, a transmission diffraction grating 71 can be incorporated at the output of the photonic band structure device as illustrated in FIG. 11. This provides a method of selecting the correct frequency at the output. Signals are input from an input waveguide 74 to the delay region 70 before reaching the grating 71. The grating pitch may be tuned to the specific frequency of operation with a free-space region 72 to allow the diffracted beams to propagate into the output waveguides 73.

Figure 12A:
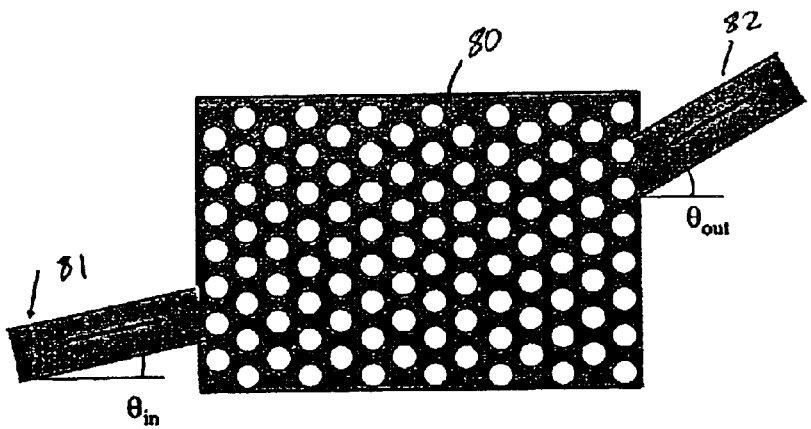
FIG. 12a shows an optical delay device according to the present invention using refraction to isolate the required wavelength.

A further alternative is shown in FIG. 12a and exploits the strong variations in the group velocity of the photonic band structure itself to refract the correct frequency to a specific angle. Owing to the large variations in group velocity around the desired region of operation a small incident angle $\theta_{in}$ provides a large refracted output angle $\theta_{out}$. This can provide very accurate frequency separation. The device shown in FIG. 12a includes an input waveguide 81, a delay region 80 and an output waveguide 82.

Figure 12B:
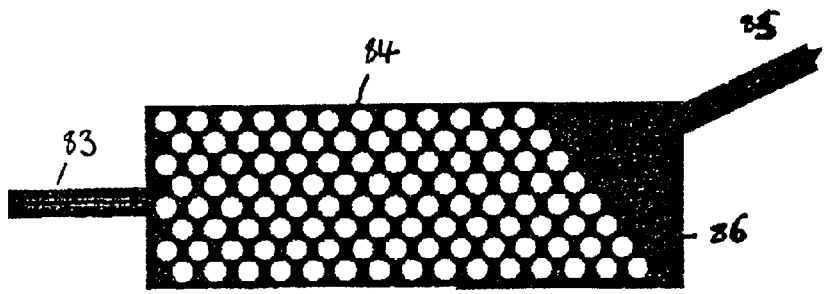

FIG. 12b shows a further example exploiting refraction. The device shown includes an input waveguide 83, a delay region 84 and an output waveguide 85. The output facet 86 of the photonic crystal delay region 84 is angled. The output beam is refracted to varying degrees in dependence on wavelength. The output waveguide 85 is positioned to receive an output beam at the wavelength of operation.

Figure 13:
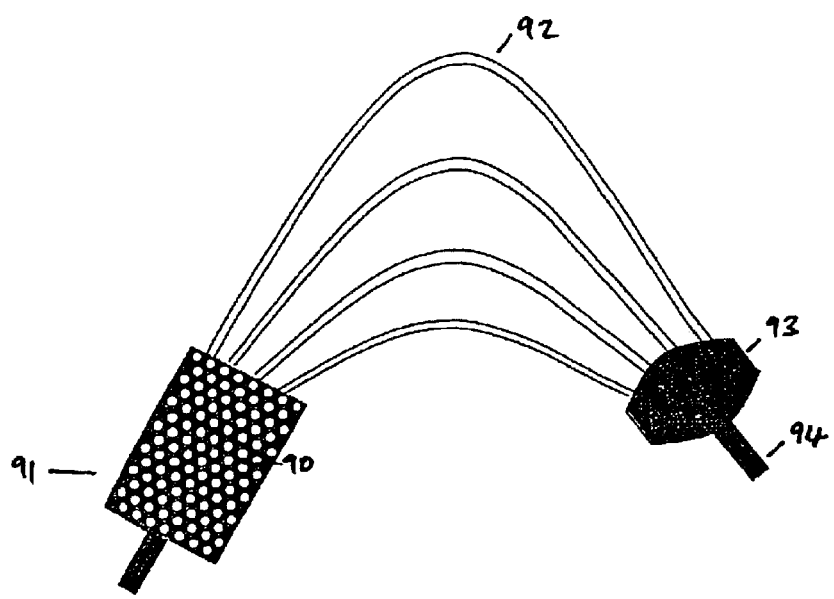
FIG. 13 shows a phase-arrayed waveguide grating including a delay region in accordance with present invention.

Another means for selection of the desired frequency is use of a phased-array waveguide grating as shown in FIG. 13. The delay region 90 having a photonic band structure is placed in a slab region of the input coupler 91. The optical signal is delayed and allowed to diverge in the delay region

90. The diverged light is coupled to the waveguides 92, which may include tapers to improve coupling efficiency. The number of waveguides and the phase difference introduced between them provides the device with the versatility to select the required frequency with the desired resolution. At the output, a free-space slab region 93 is placed so that light diffracted out of the phased array waveguide is efficiently coupled into the output waveguide 94, which is positioned at the correct location and exact tilt to couple the right frequency of light.

A further possibility is a simple optical filter as shown in FIG. 6.

Figure 14:
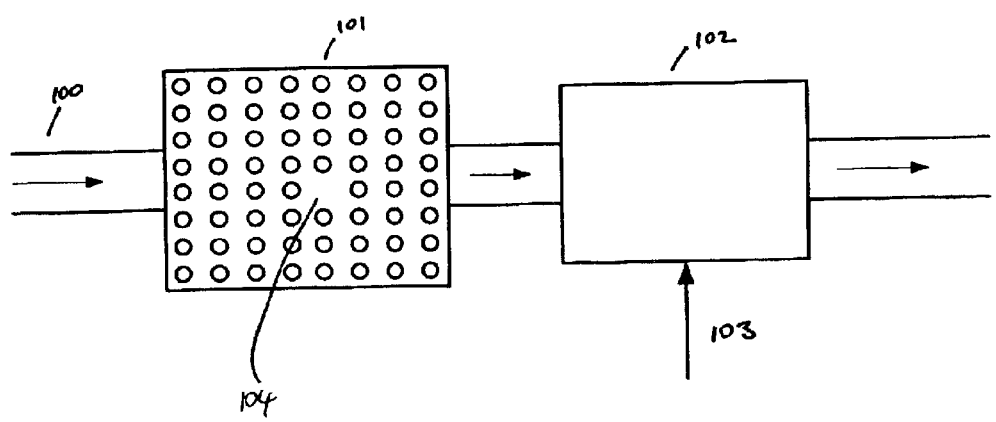
FIG. 14 is a schematic representation of an optical delay device including an optical gating device.

Another way to isolate the required wavelength is to sample the output at different times using an optical gating device, such as a Kerr cell. Different wavelengths undergo different amounts of delay and so are separated in time at the output. The gating device 102 can be very simply attached at the output of the delay device as is shown schematically in FIG. 14. FIG. 14 shows an optical input 100, a delay region 101 and a Kerr Cell 102 which is controlled by an electrical control signal 103. The Kerr Cell acts as a shutter which is opened and closed in accordance with the electrical input signal 103. The delay region includes a defect 104 which can be used to alter the band structure of the delay region and make it more sensitive to tuning measures as described below.

The sampling rate is related to the bit rate of the input optical signal. The bit rate in a telecommunications network is usually set and so the gating device can be set up for the particular network it is in. However, the lower the bit rate the longer the intervals that can be sampled by the gating device and hence the greater the power that can be collected. Reducing the bit rate therefore provides lower loss for a given time delay, and conversely a longer time delay for a given loss. In fact, the time delays for a 1 Tbit network have been shown to be more than 10 times the time delays in a 14.1 Tbit network for the same power.

All of the above examples of wavelength selection are described with reference to transmission delay regions. Clearly similar arrangements can be made with delay regions working in a reflection scheme using backward diffraction or a transmission wavelength selective element at the output.

There are a number of ways of tuning the time delay imparted to an input optical signal. For example the angle of incidence of the input optical beam relative to the structure of the delay region can be altered to alter the resultant time delay. The photonic crystal can be heated or cooled to tune the frequency response as the crystal expands or contracts. In a photonic crystal comprising an array of holes in a dielectric substrate, the holes of the photonic crystal structure may be filed with different substances or mixtures to alter their refractive index and thus alter the time delay imparted to an optical signal. The aspect ratio of the photonic crystal can also be altered to tune the time delay. The aspect ratio is directly related to the rate of change of time delay with respect to frequency, i.e. the sharpness of the band structure.

In order to be able to tune the optical delay more sensitively a defect can be introduced into the photonic crystal structure. The defect gives the delay region a higher Q factor, making it more sensitive to the tuning measures described above. The defect could, for example, be a missing region in the array as shown in FIG. 14, a displaced region or an enlarged or reduced region within the array. Alternatively, it could be a region within the array having a different refractive index to the rest of the array.

Alternatively, the defect can be formed from a superposition of two arrays. The superposition of lattices results in a Moire type structure which responds in a similar manner to a set of defects introduced into a single array and is easier to design. Having a set of defects allows light to be coupled into a defect mode more easily than for a single defect. Furthermore, having a large number of defects introduces flat bands in the band structure which allows greater optical delays to be achieved more readily.

While the present invention has been described with respect to particular example embodiments, those skilled in the art will recognize that the present invention is not limited to these specific example embodiments. Different formats, embodiments, and adaptations besides those shown and described as well as many variations, modifications, and equivalent arrangements may also be used to implement the invention. Accordingly, it is intended that the invention be limited only by the scope of the claims appended hereto.

What is claimed is:

1. An optical system comprising:
   a modulated optical signal source;
   an optical input;
   a delay region having a photonic band structure; and
   an optical output,
   wherein the optical input is adapted to couple an optical signal of a particular wavelength from the modulated optical signal source into a particular mode in the delay region such that the group velocity of the optical signal is reduced, and
   wherein the optical output includes a wavelength selective element to select said particular wavelength.

2. An optical system according to claim 1, wherein the delay region comprises a first material having a first refractive index including an array of regions having a second refractive index.

3. An optical system according to claim 2, wherein the array of regions extends over a plane in two dimensions.

4. An optical system according to claim 2, wherein the delay region is a 1-dimensional photonic crystal formed from a stack of dielectric slabs, with alternate slabs forming the array of regions having a second refractive index, or from a series of slots in a dielectric substrate.

5. An optical system according to claim 2, wherein the array of regions has an order of rotational symmetry about a point in the array of less than four.

6. An optical system according to one of claim 2, wherein the array of regions includes one or more defects.

7. An optical system according to claim 6, wherein the defects are the result of a superposition of two arrays.

8. An optical system according of claim 2, wherein the first material is silicon nitride or silicon oxynitride.

9. An optical system according to claim 1, wherein the delay region is adapted to predominantly reflect optical signals of a particular wavelength of operation.

10. An optical system according to claim 1, wherein the frequency response of the delay region is tuned by varying the temperature of the delay region.

11. An optical system according to claim 1, wherein the frequency response of the delay region is tuned by forming at least part of the delay region from a piezoelectric material and applying a potential difference across the delay region.

12. An optical system according to claim 1, wherein the frequency response of the delay region is tuned by altering the refractive index structure of the delay region.

13. An optical system according to claim 12, wherein the array of regions is formed from an array of holes in a slab of material and a composition of the material filling the holes is selected to tune the frequency response of the delay region.

14. An optical system according to claim 12, wherein either the material or the array of regions is formed from an electro-optic or magneto-optic material and a potential difference or magnetic field is applied across the delay region to tune the frequency response of the delay region.

15. An optical system according to claim 1, wherein a direction of incidence of optical signals relative to the array can be altered to obtain a different frequency response from the delay region.

16. An optical system according to claim 15, wherein the delay region is adapted to be rotated relative to the optical input and optical output.

17. An optical system according to claim 1, wherein the optical device is adapted to cause optical signals from the optical input to undergo multiple passes of the delay region.

18. An optical system according to claim 1, adapted such that the optical signals undergo a plurality of passes through the delay region.

19. An optical system according to claim 18, wherein the optical device includes waveguides, the waveguides causing multiple passes of the optical signals through the delay region.

20. An optical system according to claim 1, further comprising multiple delay regions.

21. An optical system according to claim 20, wherein the optical device includes two delay regions arranged parallel to one another, each adapted to reflect the optical signals toward the other, such that, in use, the optical signals undergo a plurality of reflections before reaching the optical output.

22. An optical system according to claim 21, wherein waveguides are positioned between the two delay regions to receive the reflected signals.

23. An optical system according to claim 1, wherein the wavelength selective element is an optical filter.

24. An optical system according to claim 1, wherein the delay region is operable to diffract optical signals.

25. An optical system according to claim 24, wherein the optical output is placed at a particular angular position relative to the optical input to receive a particular order of diffraction.

26. An optical system according to claim 1, wherein the optical input is arranged at an angle to an input or output facet of the delay region such that the optical signal is refracted.

27. An optical system according to claim 1, wherein the optical device is a phase-arrayed waveguide grating, the delay region is positioned in an input coupler, and waveguides form the wavelength selective element.

28. An optical system according to claim 1, wherein the wavelength selective element is an optical gate adapted to sample an optical output at different times.

29. An optical device comprising:
a delay region having a photonic band structure;
an optical input; and
an optical output,
wherein the optical input is adapted to couple an optical signal of a particular wavelength into a particular mode in the delay region such that a group velocity of the optical signal is reduced, and
wherein the delay region is adapted to predominantly reflect the input optical signal at the particular wavelength to allow the optical signal to be coupled into a highly dispersive mode.

30. An optical device comprising:
a delay region having a photonic band structure;
an optical input; and
an optical output,
wherein the optical input is adapted to couple optical signals into a particular mode in the delay region such that a group velocity of the optical signals is reduced, and
wherein the optical device is adapted to cause the optical signals from the optical input to undergo a plurality of passes through the delay region to thereby increase the optical path length of the optical signals in the delay region.

31. An optical device according to claim 30, wherein the optical device includes two delay regions arranged parallel to one another, each adapted to reflect the optical signals toward the other, such that, in use, the optical signals undergo a plurality of reflections before reaching an optical output.

32. A method of applying a delay to a modulated optical signal, comprising:
coupling the optical signal into a particular mode in a photonic band structure; and
selecting a part of the optical signal output from the photonic band structure based on wavelength.

33. A method according to claim 32, wherein the selecting a part of the optical signal output includes passing the optical signal output through an optical filter.

34. A method according to claim 32, wherein the selecting a part of the optical signal output includes passing the optical signal output through a diffraction grating.

35. A method according to claim 32, wherein the selecting a part of the optical signal output includes passing the optical signal output through an optical gate.

36. A method according to claim 32, wherein the selecting a part of the optical signal output includes collecting an angular portion of the optical signal output.

* * * * *